United States Patent [19]

Lewis

[11] Patent Number: 4,968,131
[45] Date of Patent: * Nov. 6, 1990

[54] VISUAL ACUITY TEST DEVICE AND METHOD OF PREPARING SAME

[75] Inventor: John M. Lewis, Crestwood, Mo.

[73] Assignee: Stereo Optical Company, Inc., Chicago, Ill.

[ * ] Notice: The portion of the term of this patent subsequent to Aug. 8, 2006 has been disclaimed.

[21] Appl. No.: 329,974

[22] Filed: Mar. 29, 1989

Related U.S. Application Data

[62] Division of Ser. No. 912,398, Sep. 26, 1986, Pat. No. 4,854,695.

[51] Int. Cl.$^5$ .............................................. A61B 3/02
[52] U.S. Cl. .................................................... 351/239
[58] Field of Search ................ 351/296, 239, 201, 209

[56] References Cited

U.S. PATENT DOCUMENTS

| | | | |
|---|---|---|---|
| 1,412,902 | 4/1922 | Tallman | 351/239 |
| 1,999,054 | 4/1935 | Lee | 351/239 |
| 3,011,394 | 12/1961 | Sherman et al. | |
| 3,738,099 | 6/1973 | Tanaka | 350/331 R |
| 3,922,667 | 11/1975 | Ueda et al. | 350/333 |
| 3,982,239 | 9/1976 | Sherr | 350/333 |
| 4,607,923 | 8/1986 | Task et al. | 351/239 |
| 4,854,695 | 8/1989 | Lewis | 351/246 |

Primary Examiner—Rodney B. Bovernick
Assistant Examiner—J. Ryan
Attorney, Agent, or Firm—Lockwood, Alex, Fitzgibbon & Cummings

[57] ABSTRACT

A visual acuity testing device and method of preparing same are provided, the device being in the form of an optotype as well as a series of optotypes of the same nature, each of which is defined according to a rectangular optotype gridwork including a plurality of rectangular unit areas of contrasting colors or differing contrast properties that are varied in coloration or contrast as desired in order to form a set of optotype characters that exhibit similar peripheral shapes that vary from one another to define readily recognizable optotype characters.

15 Claims, 2 Drawing Sheets

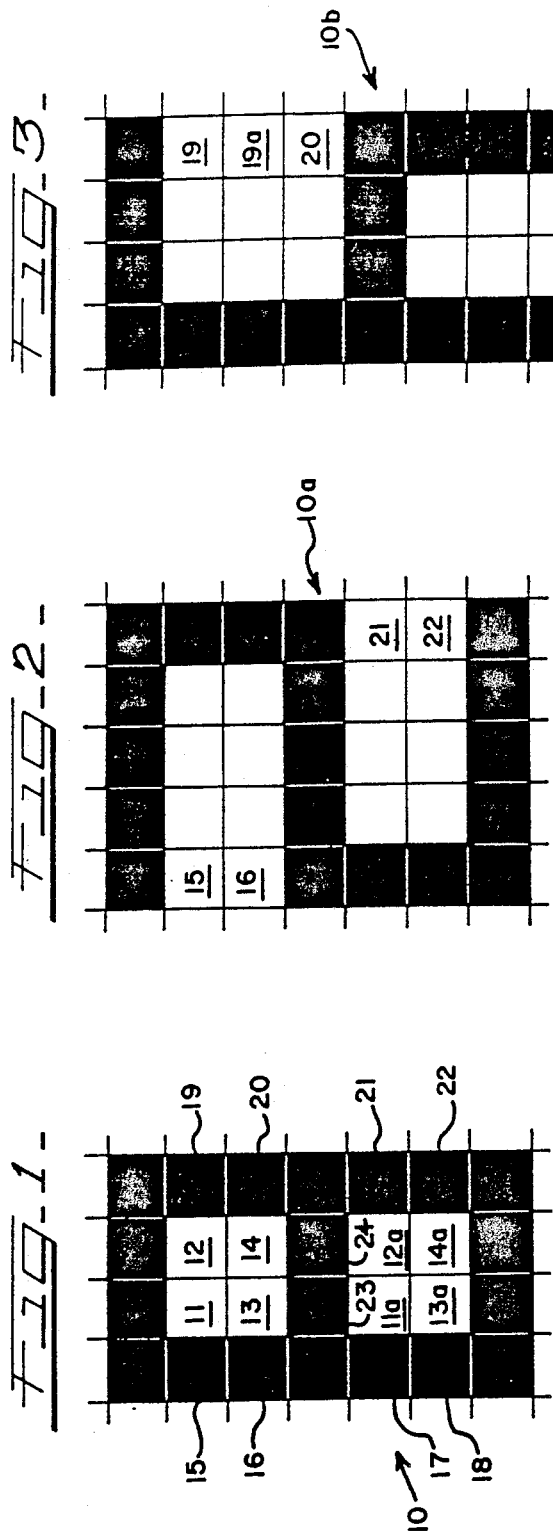

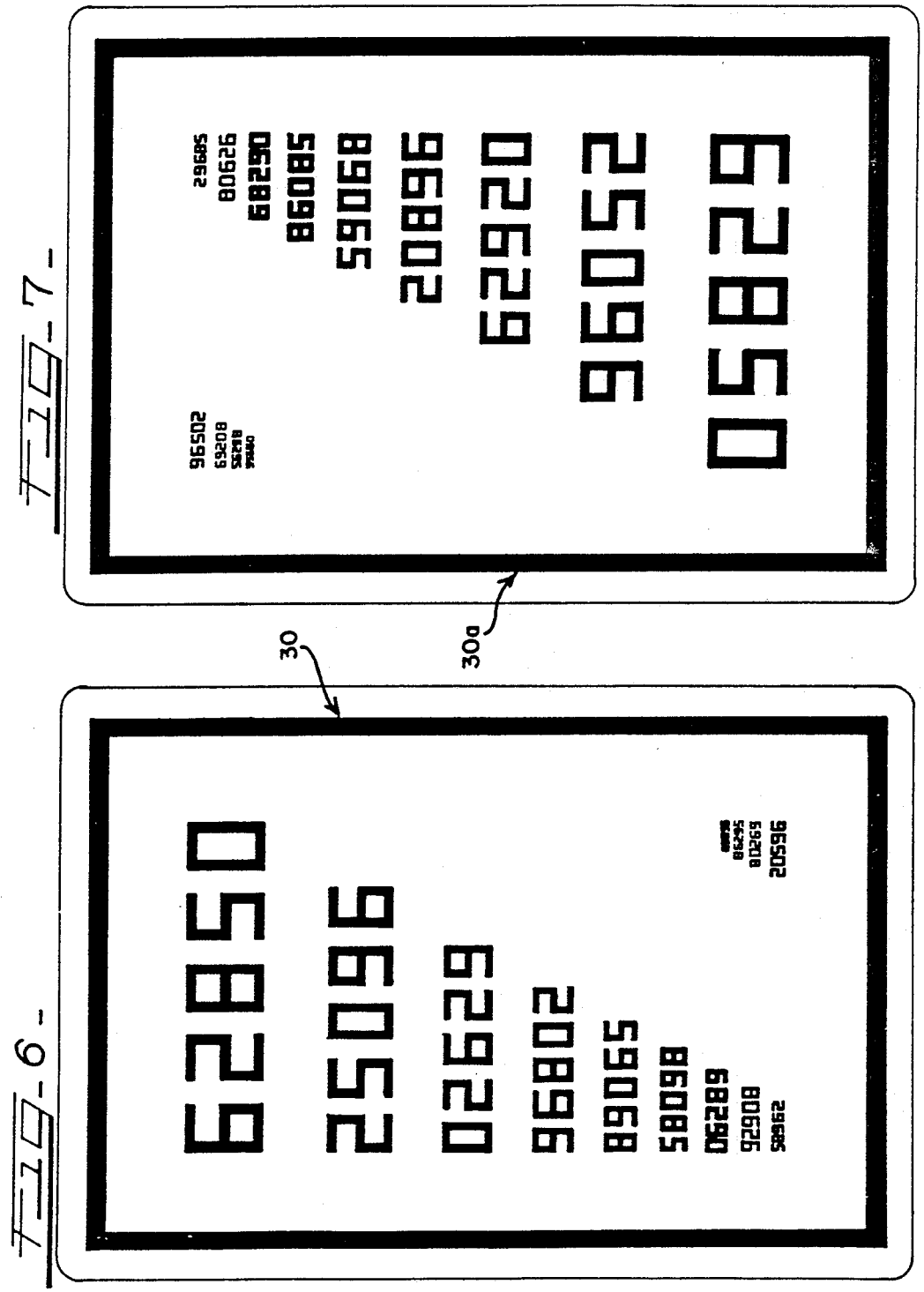

VISUAL ACUITY TEST DEVICE AND METHOD OF PREPARING SAME

This is a division, of application Serial No. 912,398, filed Sept. 26, 1986 now U.S. Pat. No. 4,854,695.

Background and Description of the Invention

The present invention generally relates to devices for determining visual acuity and more particularly to visual acuity testing devices that are especially well suited for standardization, accuracy and reproduceability. Included is an optotype format that presents a uniform overall appearance which is modifiable in a generally uniform manner in order to create different numerals that embody many advantageous properties while providing a testing scheme that is more directly geared toward evaluating the visual acuity of the subject and not his or her ability to recognize differences in shapes or patterns of shapes.

Visual acuity charts which utilize letters as optotypes have been in standard clinical use since Snellen introduced his acuity test in 1862. The visual acuity test chart may be used in many ways. Determination of lens correction, determining degree of observation of spatial detail, detection of impairment of central vision, assessment of the effects of medical or surgical therapy, progressive changes in impaired vision, screening testing, qualifying testing as well as evaluation of designs for environmental lighting and display lighting are examples of the many uses to which visual acuity testing is applied.

Since the early developments by Snellen, other optotypes and combinations thereof have been used. Of these, the most widely used are the Sloan letters and the Landolt ring. In each instance these systems have been attempting to improve the standardization of acuity tests by incorporating use of various letters or designs as optotypes depending on the difficulty of character recognition. Those acuity tests which incorporate different letters as optotype characters are limited in uniformity by having variability of optotype recognition difficulty. Standardization in this area of uniformity is very important because, for example, when a patient is referred from one practitioner to another, the results of the two examinations should be comparable. Standardization of degree of difficulty related to optotypes utilized is required to make such comparisons meaningful. Such standardization is also needed to evaluate changes with time, as well as those changes resulting from injury or disease. Still further, standardization is essential in investigating the effects of therapy.

Each time that different letters or designs are incorporated in visual acuity charts, substantial variations in optotype shape as well as difficulty result. Initially, the Snellen illiterate E was intended to eliminate such variations. The Landolt rings were also intended to eliminate such variations. Sloan et al, in an attempt to standardize testing so as to achieve meaningful long range results, made use of the alphabetical letters C, D, H, K, N, O, R, S, V, and Z. None of these efforts have resulted in complete standardization and, actually, it has been found that certain of these optotypes are better suited for certain testing purposes than other optotypes thus actually thwarting standardization efforts.

With regard to the Snellen illiterate E, such an optotype requires the individual being tested to not only be able to recognize the optotype but, in addition, to communicate to the examiner the optotype's orientation in space. Acuity tests which utilize character orientation as a distinguishing factor creates confusion for individuals who have difficulty in distinguishing right from left. Using various letters as optotypes are of questionable reliability when testing pre-school aged children, or individuals from cultures not familiar with Roman letters. These shortcomings apply directly for example, to the Sloan et al series of letters. Additionally, the Sloan et al letters provide an optotype format that embodies units of differing shapes since they utilize curves and diagonal lines as well as straight horizontal and vertical lines, thus increasing the complexity of evaluating testing results for the many different purposes required. The Landolt rings are often considered suitable as a primary standard but impractical for clinical testing. Because of the similarity of the rings, it is difficult for the individual being tested to keep his of her place on a line of rings. Still further, such rings necessitate specific instructions as to what the person being examined is expected to see or note, as well as necessitating error inducing steps such as pointing or verbal description to establish results.

The optotypes of the present invention present the same overall external configuration thereby eliminating the variable of character recognition based on external shape. This requires the individual being tested to be able to identify the optotype by the presence or absence of short linear segments. Preferably, the present invention makes use of Arabic numbers in acuity testing thereby facilitating the testing of young children who often learn to recognize numbers long before they have reliably mastered the alphabet. Illiterate individuals, in general, are also able to identify numbers much more easily than letters. This also applies to individuals from other cultures who may not be familiar with the English alphabet. The format of the basic optotype pattern of this invention is such that there are no curves or diagonal lines. All of the lines are straight and are either horizontal or vertical. In addition to being more suitable for standardization and accuracy enhancement, this format enables the use of these optotypes on automated visual acuity testing devices which utilize cathode ray tube types of displays, high resolution video monitors, and the like.

An additional feature and advantage of the new and improved optotypes and method of forming same according to the present invention resides in the potential for chart inversion. Due to the design of the optotypes and the selection of certain numbers having common characteristics, it is possible, for example, to invert a test chart presenting a set optotype sequence in order to thereby confront the individual undergoing testing with an entirely different sequence of numbers. This feature is particularly advantageous in near acuity testing. After testing the first eye, the near test card or chart is inverted and the second eye is tested with a new series of numbers thereby eliminating the factor of memorization which is often present when testing the second eye in this type of near acuity testing.

Further advantageous features of the present invention include presenting optotypes that have uniform wall thicknesses throughout, which enhances the validity of the visual acuity test results. Another important and particularly useful advantage is the ability of the optotype characters of the present invention to be used as components of a binocular-type of right eye and left eye fusion test that is readily administered with a good degree of accuracy.

Summary of the Invention

The present invention relates generally to improved optotypes, charts, slides, cards and other forms of visual displays that incorporate such optotypes, as well as to the method of preparing such visual displays. Each optotype character is formed from a basic gridwork of rectangular configuration that is subdivided only horizontally and vertically into rectangular units that are of equal area and that are of a color that highly contrasts with the gridwork background. The method of preparing each optotype character involves the selective omission or color or contrast change of certain of these uniformly sized units to establish selected optotype characters which completely utilize the horizontal and vertical dimensions of the gridwork. Preferably, the optotype gridwork includes a ratio of horizontally aligned uniform rectangular units to vertically aligned uniform rectangular units on the order of between about 5 to 7 and about 4 to 9. The preferred basic optotype format is recognizable as the number 8, and this selective omission or color or contrast change of uniform rectangular units transforms the basic optotype format into patterns that are recognizable as other numbers.

It is accordingly a general object of the present invention to provide an improved visual acuity test device both in the form of an optotype as well as a chart or other visual display utilizing a plurality of such optotypes, and to provide a method for generating or preparing each optotype or visual display.

Another object of the invention is to provide a method of forming an optotype from a gridwork composed of a plurality of horizontally and vertically aligned uniformly sized and shaped rectangular units and selectively omitting certain of such units from the grid to thereby establish a variety of characters which retain the overall rectangular configuration and uniform dimensions of the grid.

Another object of the present invention is to provide a new and improved basic form of optotype which permits standardization of results derived from multiple purpose testing.

Another object of the present invention is to provide optotypes that have substantially the same external configuration thereby eliminating character discernment based only on external shape and requiring the individual being tested to be able to identify the character represented by the optotype by the presence or absence of uniform units or segments.

Another object of the present invention is to provide an improved optotype which young children, illiterate individuals as well as individuals from other cultures can more readily and successfully identify thereby facilitating accurate testing of such individuals.

Another object of the invention is to provide an improved optotype system that exhibits excellent correlation with currently standard acuity test systems such as those utilizing Sloan or Snellen letters.

Brief Description of the Drawings

The features of the present invention which are believed to be novel are set forth with particularity in the appended claims. The invention, together with further objects and advantages thereof, may best be understood with reference to the following description taken in conjunction with the accompanying drawings, in the several figures of which like reference numerals identify like elements, and in which:

FIG. 1 is a plan view of the preferred optotype format of the present invention, this optotype format being recognizable as the number 8;

FIG. 2 is a plan view of an optotype character of the present invention derived from the basic optotype format that follows a grid pattern having a ratio of horizontal grid units to vertical grid units different from that of FIG. 1, the illustrated optotype character being recognizable as the number 2;

FIG. 3 is a plan view of another optotype character derived from still another optotype format that follows a grid pattern having a ratio of horizontal grid units to vertical grid units different from that of FIGS. 1 and 2, the illustrated optotype character being recognizable as the number 6 and as the number 9 when inverted;

FIG. 4 is a plan view of the basic optotype characters in the form of numbers which are preferably established by the optotype format of the present invention;

FIG. 5 illustrates the optotype characters that can be established from the basic optotype grid pattern of the present invention but which do not provide all of the features desired of the optotype characters according to the present invention;

FIG. 6 is a plan view of a testing chart or other visual display utilizing the optotype format and optotype characters of the present invention; and FIG. 7 is a plan view of the chart or visual display of FIG. 6 when same is inverted but otherwise unmodified.

Description of the Particular Embodiments

FIG. 1 illustrates a preferred form of the optotype gridwork or format according to the present invention. This optotype gridwork, generally designated as 10, is of rectangular configuration with the vertical axis being of greater length than the horizontal axis. The optotype gridwork 10 is formed from a series of vertically and horizontally aligned uniform rectangular units which are of equal dimensions and area. Basically, the preferred characters to be depicted by modifying each optotype format of the present invention are identifiable as Arabic numbers. While other optotype characters may be utilized, the invention will be described in its preferred form, namely, utilizing Arabic numbers.

The character that is identifiable as an 8 in FIG. 1 is formed from the optotype gridwork 10 by the omission of or transformation of selected character-forming or colored uniform rectangular units such that the areas that are thereby omitted or transformed form a portion of the background of the gridwork. For purposes of illustration, each character-forming uniform rectangular unit retained or included in the optotype gridworks illustrated in the accompanying drawings is black while each omitted or background uniform rectangular unit is white, although other color combinations can be used. The preferred shape of each uniform rectangular unit is square, as illustrated in the drawings, each such square being of a uniform size. In preparing the character 8 illustrated in FIG. 1, the internally located unit squares 11, 12, 13 and 14 as well as 11a, 12a, 13a and 14a are omitted or removed from the optotype gridwork 10, that is they are background units, while the character-forming black units 15, 16, 17, 18, 19, 20, 21, 22, 23 and 24 are retained along with the other character-forming black units illustrated, which are not ever omitted or transformed to background units when practicing the invention.

By transforming selected character-forming units 15 through 24 into background units, such as by changing their color from black to white, Arabic numbers other than 8 are formed. For example, by transforming units 15, 16, 21 and 22 from black to white, the numeral 2 is formed, as is generally shown in FIG. 2 with respect to a different optotype gridwork 10a. By transforming units 17, 18, 19 and 20 of gridwork 10 in FIG. 1 from black to white, the numeral 5 is formed. By transforming units 19 and 20 from black to white, the numeral 6 is formed; by transforming units 17 and 18 from black to white, the numeral 9 is formed; and by transforming units 23 and 24 from black to white, the numeral 0 is formed. These various numerals are illustrated in FIG. 4. In each case, the transformations are of one or two sections that include, for gridwork 10, two units.

It will be noted in particular that the character 8 assumes the rectangular configuration and dimensions of optotype gridwork 10. This is an important aspect of the invention since it contributes to the standardization of size, overall shape and recognition attributes of the characters used in these vision testing optotypes. With respect to this important aspect of standardization, because the optotype gridwork allows for formation of optotype characters having the same overall external configuration, the invention minimizes variations in recognition difficulty from one character to another. Additionally, the numeric optotypes of the present invention have relative dimensions similar to numerals used in LCD or LED displays and are conveniently displayed in an accurate manner on cathode ray tube systems and the like.

While the optotype gridwork 10 of FIG. 1 utilizes a 4 to 7 ratio of horizontal units to vertical units, FIG. 2 illustrates an optotype gridwork 10a having a 5 to 7 ratio. The optotype gridwork 10a of FIG. 2 is of the same relative height as the relative height of optotype gridwork 10 of FIG. 1, but its relative width is one unit wider. The form of the optotype gridwork 10a that is depicted in FIG. 2 is the numeral 2 in which the peripheral units 15, 16, 21 and 22 have been transformed from black character units to white background units.

FIG. 3 illustrates another form of optotype gridwork 10b of the present invention utilizing a ratio of horizontal units to vertical units of 4 to 9. This optotype gridwork 10b of FIG. 3 is of the same relative width as the relative width of optotype gridwork 10 of FIG. 1, but its relative height is two units greater. The form of the optotype gridwork 10b that is depicted in FIG. 3 is the numeral 6 in which the peripheral units 19, 19a and 20 have been transformed from black character-forming units to white background units.

The preferred range of variation of the ratio of horizontal units to vertical units that are included in optotype gridworks of the present invention is illustrated by the gridworks depicted in FIGS. 1, 2 and 3. As previously described, FIG. 1 illustrates the basic preferred form of optotype gridwork, which has a ratio of horizontal to vertical units of 4 to 7 (or 0 57). FIG. 2 illustrates the preferred upper limit of the horizontal to vertical ratio, which is 5 to 7, (or 0.72). FIG. 3 illustrates the preferred lower limit of the horizontal to vertical ratio, which is 4 to 9 (or 0.44). In all instances, the optotype characters formed from these optotype grids assume the general rectangular configuration and dimension ratio of their particular gridwork.

It will be noted that the uniform rectangular units that are transformed in color in order to form each desired numerical character take on a predetermined pattern of transformed segments that include two or three uniform rectangular units. Each transformed segment can be characterized as defining an area having a unit width by a unit height of 1 by 2, 2 by 1, 3 by 1, or 1 by 3. In the preferred embodiments, the "lines" of each optotype character are of uniform thickness, namely, one unit thick. The design of each of these optotype gridworks is such that none of the optotype characters include curved or diagonal lines. All of the lines are either horizontal or vertical, and spacing between these lines is generally uniform. These features enable the use of these optotype characters on automated visual acuity testing devices including those which utilize cathode ray tubes and high resolution video monitors.

The subject optotype characters establish an acuity test that is valid when compared with the conventionally used Snellen and Sloan visual acuity tests. The size of the preferred subject optotype characters have been established to be approximately seven minutes of an arc in height and four minutes of an arc in width in order to be equivalent from a testing viewpoint to a Sloan or a Snellen optotype test pattern with dimensions of five minutes of an arc by five minutes of an arc.

Most acuity tests that are in general use today lack the appropriate design parameters necessary to conveniently record and store the acuity information obtained in a computer format. Due to the design of the subject optotypes, the standard LogMAR system may be utilized in modified form to obtain decimal notations which facilitate data entry and retrieval with the aid of a computer. An equal number of optotype characters per line facilitates the recording of acuity in decimal notation, and each character can be assigned a standard value. For example, in LogMAR notation, 20/25 vision is denoted as 0.1. The present invention permits assigning a value of 1.0 thereto and a value of 0.2 for each optotype character of a five-character line, thereby providing decimal notation for each vision test position. Such decimal notation is especially complementary to acuity test data computer entry and computer analysis of acuity test results.

FIG. 4 illustrates the preferred Arabic numbers constituting the preferred characters to be depicted by the optotype gridworks of the present invention. These numbers are selected because of their capability of readily assuming the rectangular configuration of the optotype gridwork and because each of them substantially fills the horizontal and vertical dimensions of the optotype gridwork. In addition, as will be described in greater detail in connection with FIG. 7, these optotype gridwork numbers formed in accordance with the method of the present invention, when inverted, either retain the same numerical configuration or depict another number of the same series. For example, when the optotype character 2 is inverted, it remains a 2, and inverted optotype character 5 remains a 5. Likewise, the optotype characters 8 and 0 remain as an 8 and 0, respectively, when inverted. When the optotype character 6 is inverted, it appears as the optotype character 9, while the inverted optotype character 9 is seen as the optotype character 6.

The numbers 1, 3, 4 and 7 of FIG. 5 which can be formed from optotype gridworks according to the present invention preferably are not included in testing charts or other types of usual displays according to this invention. Except for number 3, these numbers do not meet the criteria set forth above, such as utilizing characters which generally fill the rectangular configuration and dimensions of the optotype gridworks by omitting only one or two colored or character-forming sections of uniform rectangular units. The number 1 omits five such sections, the number 4 omits three sections, and the number 7 omits four sections, which omissions render each of these numbers too easily distinguishable from other numbers in the series. While the number 3 meets these criteria, it is preferably not used because of its inability to be inverted and still retain a numerical form and because of its asymmetry in having both of its non-colored or background sections on the same side of the character which renders the 3 more easily distinguishable from the other preferred optotype numbers. It will be understood, however, that the number 3 may be used if these shortcomings can be tolerated for a particular testing chart or other visual display.

The method of preparing the optotypes of the present invention includes the selection of a gridwork rectangular configuration, such as on the order of the three gridworks shown in FIGS. 1 through 3. Such selection can include variables depending upon the particular form or shape of character or characters to be depicted by the optotypes. Once the gridwork has been selected, it must then be sub-divided into rectangular units of equal dimensions and area so as to establish uniformity in the formation of the selected characters to be depicted. Then the sub-divided gridwork is utilized to form each selected character by changing the color or contrast characteristics of certain rectangular units of the gridwork, thereby transforming the gridwork into the character.

The rectangular units thus transformed are located peripherally within the gridwork, with these peripheral rectangular units being no more than three abreast. A similar, but internal, section of rectangular units is also included. Also, the ratio of horizontally aligned rectangular units to vertically aligned rectangular units in a suitable gridwork is between 5 to 7 and 4 to 9, most preferably this ratio being 4 to 7. Still further, each character to be depicted should give an overall appearance that approximates the rectangular configuration and peripheral dimensions of the gridwork. Suitable preferred characters are the numbers 2, 5, 6, 8, 9 and 0 because they present the recognizably different characters that have respective external appearances that are so similar that uniformity of testing conditions is enhanced.

FIG. 6 illustrates a conventional form of visual acuity testing chart 30 including rows of optotype characters that are progressively graduated as to size in order to cover the typical range of sizes needed for testing visual acuity. The optotype characters of FIG. 6 are those previously described in conjunction with FIGS. 1 through 4. In general, the character size progression from line to line is determined by the known and often used multiplication factor of 1.2589; that is, adjacent lines have respective type sizes that exhibit a size ratio therebetween that generally equals this multiplication factor.

FIG. 7 illustrates the chart 30 of FIG. 6 in inverted form. This inverted chart 30a is most beneficially used in testing near vision. For example, the chart 30 of FIG. 6 may be used initially to test the near vision of the left eye of a patient or subject and may be quickly inverted to take on the appearance of chart 30a for use in testing the near vision of the right eye while providing a different numeric sequence, thus avoiding inaccurate test results due to memorization of the number sequence by the patient or subject. Of course, if the testing chart or material contained therein is to be projected from a film strip, slide or other suitable projection equipment, or is to be included within a cathode ray tube display or the like, the inverted form of the chart may be separately provided.

The use of numerical characters in acuity testing facilitates the testing of young children who often learn to recognize numbers long before they have reliably mastered the alphabet. Illiterate individuals, who in general are also able to identify numbers more readily than letters, as well as individuals from other cultures who may not be familiar with the English alphabet, are also more effectively tested. Also, there is no need for the individual being tested to communicate to the examiner the optotype's orientation in space which is a requirement of other optotype systems. Each optotype character according to the invention has a similar external shape and does not include curves, angles or large gaps, which minimizes the variable of recognition of gross variables in external configuration. These attributes of the optotype characters according to the present invention enables the use of these optotype characters on automated visual acuity testing devices which utilize visual displays including cathode ray terminals having high resolution video monitors. For example, a single optotype character or series thereof could be displayed on the screen, and such character or characters could be changed in random fashion or according to a predetermined fashion in order to check for eye strain or damage at the beginning, end or other stage of a work day for a computer or word processor operator. It would even be possible to vary the size of the character or characters by appropriate software.

The optotype system according to the present invention is also particularly useful in conducting so-called binocular tests of the fusion abilities of the test subject. By having this basic test incorporate optotype characters according to the present invention, the following exemplary arrangement provides a particularly effective and easily administered binocular vision test. For example, one side of a stereo slide would include a numeral 2 optotype character according to the invention while the other side of the stereo slide would include a numeral 5 optotype character. A "healthy" pair of eyes would see a numeral 8 optotype character because the test subject's eyes would "fuse" the 2 and the 5 into an 8, whereas a test subject having poor fusion abilities would see a 2 or a 5 under certain conditions. Other combinations of the optotype characters according to the invention would achieve similar results. This advantageous binocular test system is greatly facilitated because of the overall uniformity of the optotype characters as discussed in greater detail herein.

While particular embodiments of the invention have been shown and described, it will be obvious to those skilled in the art that changes and modifications may be made therein without departing from the invention in its broader aspects, and, therefore, the aim of the appended claims is to cover all such changes and modifications as fall within the true spirit and scope of the invention.

I claim:

1. A device for determining visual acuity, comprising:

rectangular optotype gridwork means for determining visual acuity of literate or illiterate individuals with enhanced standardization, said optotype gridwork means being sub-divided into a plurality of uniformly sized and shaped rectangular unit areas, each said unit area having dimensions equal to corresponding dimensions of every other one of said unit areas;

an optotype character defined within said optotype gridwork means by selectively varying the coloration or contrast properties of only generally horizontally aligned and generally vertically aligned uniformly sized and shaped rectangular unit areas in order to provide background rectangular units of one color or contrast property and in order to provide character-forming rectangular units of a contrasting color or different contrast property, said generally horizontally aligned and generally vertically aligned character-forming rectangular units being positioned with respect to each other in order to form a recognizable optotype character;

the character-forming rectangular units include peripheral and internal ones of said uniformly sized and shaped rectangular unit areas of said optotype gridwork means that, when combined, form the numeral 8 character;

selected ones of said character-forming rectangular units define sections that, when replaced by background rectangular units, define characters other than the numeral 8;

not more than two of said sections are replaced by background sections of equal size and shape to define said other characters; and whereby said peripheral character-forming rectangular units of each numeral 8 character and any of said other characters define only characters having substantially the same external dimensions and configuration in order to thereby provide means for minimizing variations in recognition difficulty from one of said characters to another of said characters.

2. The device according to claim 1, wherein said other characters are selected from the numbers 2, 5, 6, 9 and 0.

3. The device according to claim 1, wherein said horizontally aligned rectangular unit areas and said vertically aligned rectangular unit areas of said optotype gridwork means have a relative relationship to each other defined as a ratio between about 5 to 7 and about 4 to 9, said optotype gridwork means thereby establishing visual acuity testing means for generally approximating test equivalency with conventionally used Snellen or Sloan visual acuity testing means.

4. The device according to claim 3, wherein said ratio is about 4 to 7.

5. The device according to claim 1, wherein said sections are defined by at least two adjacent ones of said uniformly sized and shaped rectangular unit areas.

6. A device for determining visual acuity, comprising:
optotype means for testing visual acuity of literate or illiterate individuals with enhanced standardization, said optotype means including a plurality of rectangularly shaped optotype characters progressively graduated as to size and selectively positioned in a pattern for testing visual acuity;

each said optotype character being defined by a rectangular optotype gridwork sub-divided into a plurality of uniformly sized and shaped rectangular unit areas, each said unit area having dimensions equal to corresponding dimensions of every other one of said unit areas;

each said optotype character of the optotype testing means is defined within said optotype gridwork by selectively varying the coloration or contrast properties of only generally horizontally aligned and generally vertically aligned uniformly sized and shaped rectangular unit areas in order to provide background rectangular units of one color or contrast property and in order to provide character-forming rectangular units of a contrasting color or different contrast properties, said character-forming rectangular units being positioned with respect to each other in order to form a recognizable optotype character;

the character-forming rectangular units include peripheral and internal ones of said uniformly sized and shaped rectangular unit areas of said optotype gridwork that, when combined, form the numeral 8 character;

selected ones of said character-forming rectangular units define sections that, when replaced by background rectangular units, define characters other than the numeral 8;

not more than two of said sections are replaced by background sections of equal size and shape to define said other characters; and whereby said peripheral character-forming rectangular units of each numeral 8 character and any of said other characters define only characters having substantially the same external dimensions and configuration in order to thereby provide means for minimizing variations in recognition difficulty from one of said characters to another of said characters.

7. The device according to claim 6, wherein said horizontally aligned rectangular unit areas of said optotype gridwork means and said vertically aligned rectangular unit areas have a relative relationship to each other defined as a ratio between about 5 to 7 and about 4 to 9, said optotype gridwork means thereby establishing visual acuity testing means for generally approximating test equivalency with conventionally used Snellen or Sloan visual acuity testing means.

8. The device according to claim 7, wherein said ratio is about 4 to 7.

9. The device according to claim 6, wherein said plurality of optotype characters of said pattern are each recognizable characters when inverted.

10. The device according to claim 6, wherein said pattern of optotype characters form an optical test chart.

11. The device according to claim 6, wherein said pattern of optotype characters are defined by a programmable visual display.

12. The device according to claim 6, wherein said sections are defined by at least two adjacent ones of said uniformly sized and shaped rectangular unit areas.

13. A method of forming optotypes for testing vision, said method comprising:
selecting an optotype gridwork of rectangular configuration;

sub-dividing said optotype gridwork into a plurality of uniformly sized and shaped rectangular unit areas, each said unit areas having dimensions equal to corresponding dimensions of every other one of said unit areas;

selectively varying the coloration or contrast properties of certain of the uniformly sized and shaped rectangular unit areas in order to provide background rectangular units of one color or contrast property and in order to provide character-forming rectangular units of a contrasting color or different contrast property;

positioning said character-forming rectangular units with respect to each other in order to form recognizable optotype characters, said positioning step including horizontally aligning a number of the rectangular unit areas and vertically aligning a number of rectangular unit areas;

said positioning step includes combining peripheral and internal ones of said generally horizontally aligned and generally vertically aligned uniformly sized and shaped character-forming color rectangular units which form the numeral 8 character and replacing one or more selected sections of character-forming color rectangular units with background rectangular units to define other characters;

said replacing step includes replacing not more than two of the character-forming sections, said replacing resulting in the formation of background sections of size and shape equal to said character-forming sections; and said positioning and replacing steps provide peripheral character-forming rectangular units that define only characters having substantially the same external dimensions and overall configuration in order to thereby minimize variations in recognition difficulty from one character to another character and in order to provide characters of enhanced standardization.

14. The method according to claim 13, wherein said other characters include numeral characters 2, 5, 6, 9 and 0.

15. The method according top claim 13, wherein said sections are defined by at least two adjacent ones of said uniformly sized and shaped rectangular unit areas.

* * * * *